(12) United States Patent
Lim

(10) Patent No.: US 6,259,112 B1
(45) Date of Patent: Jul. 10, 2001

(54) APPARATUS AND METHOD FOR DETERMINING IMAGING QUALITY IN A COMPUTED RADIOGRAPHY SYSTEM

(75) Inventor: Arthur J. Lim, Menlo Park, CA (US)

(73) Assignee: Lumisys, Inc., Sunnyvale, CA (US)

( * ) Notice: Subject to any disclaimer, the term of this patent is extended or adjusted under 35 U.S.C. 154(b) by 0 days.

(21) Appl. No.: 09/181,632

(22) Filed: Oct. 28, 1998

(51) Int. Cl.[7] ............................................. G01N 23/04
(52) U.S. Cl. ...................... 250/581; 250/484.4; 250/582; 250/591; 250/271
(58) Field of Search ........................... 250/581, 484.4, 250/582, 591, 271

(56) References Cited

U.S. PATENT DOCUMENTS

| | | |
|---|---|---|
| 5,056,130 | 10/1991 | Engel .................................. 378/207 |
| 5,095,431 | 3/1992 | Feldman et al. ................. 364/413.13 |
| 5,236,363 | 8/1993 | Sandrick et al. ...................... 434/267 |
| 5,357,118 * | 10/1994 | Fukuoka et al. .................. 250/484.4 |
| 5,539,799 | 7/1996 | Schulze-Ganzlin et al. ........ 378/207 |
| 5,544,157 | 8/1996 | Wenstrup et al. ....................... 378/18 |
| 5,611,958 * | 3/1997 | Takeuchi et al. ..................... 250/271 |
| 5,877,508 * | 3/1999 | Arakawa et al. ................. 250/484.4 |

* cited by examiner

Primary Examiner—Constantine Hannaher
Assistant Examiner—Andrew Israel
(74) Attorney, Agent, or Firm—Thomas Schneck

(57) ABSTRACT

A method of ascertaining imaging quality in a computed radiography (CR) system includes providing a substrate having fluorescent test pattern disposed thereon. The substrate is disposed in place of the standard storage-phosphor screen and scanned as if reading out a storage screen. The detected signals form a read-out image which is then compared against the test pattern to judge image quality.

22 Claims, 4 Drawing Sheets

APPARATUS AND METHOD FOR DETERMINING IMAGING QUALITY IN A COMPUTED RADIOGRAPHY SYSTEM

TECHNICAL FIELD OF THE INVENTION

The invention relates generally to imaging systems and more particularly to determining the imaging quality in a computed radiography imaging system.

BACKGROUND ART

In computed radiography (CR) systems, an X-ray image is produced by exposing a special storage-phosphor screen to X-rays which have been attenuated by passing through an object (usually a portion of the human body) to be imaged. The image is captured in the storage-phosphor screen. The storage mechanism involves exciting the electrons in the atoms comprising the screen to higher meta-stable energy states. The energy state varies depending on the amount of attenuation experienced by the X-rays as they pass through the body. Each electron, being in a meta-stable state, can be stimulated back to its ground state by the application of a sufficient excitation energy, and in doing so emits a photon of visible light, usually blue.

Thus, the stored image is "read" from the screen by scanning the screen with a laser beam of a specific wavelength. The emitted photons can be detected by a detector, and by blocking the stimulating wavelengths of the laser from the detector, the detected signals can be processed to reconstruct the image.

It is important that the CR system be properly calibrated and tested on a regular basis to ensure an accurate rendering of images. Testing and adjusting the image quality performance of the imaging sub-system typically requires imaging one or more test patterns and inspecting the readout image. Performance indicators of interest include: resolution, geometric accuracy, uniformity, signal accuracy and added noise. Resolution performance can be measured with a variety of commercially available resolution patterns. Typically these resolution patterns consist of arrays of thin lead strips of varying widths at varying intervals. Signal accuracy can be measured by various step wedge phantoms which provide varying amounts of X-ray attenuation. Uniformity can be measured by evaluating uniformly exposed portions of the image. Geometric accuracy requires imaging a radio opaque pattern of known dimensions. While a small object such as a circle or a square could be used to measure the aspect ratio of the image, measuring the geometric image over the entire image would require a test pattern equal to the size of the screen.

While many prior art test systems and methods are known, it is interesting to note that such systems involve variations of a central thesis, namely imaging a phantom, or some test object, and evaluating the resulting read-out image. For example U.S. Pat. No. 5,056,130 describes a calibrator comprised of a set of interchangeable pieces. The pieces have known different densities, thus permitting the assembly of configurations of known size and densities for calibrating a computerized tomographic system.

U.S. Pat. No. 5,095,431 discloses a calibration method for an X-ray scanner. The method includes positioning a non-circular shaped standard between the X-ray source and a plurality of detectors. A series of attenuation measurements are made for each of a number of principle angular positions of the standard. The resulting data is then analyzed to produce calibration curves of the X-ray system.

U.S. Pat. No. 5,236,363 describes an improved phantom having two X-ray attenuation regions, one region formed within the other. The phantom is capable of simulating a human bladder (inner region) that is surrounded by pelvic bone (outer region).

U.S. Pat. No. 5,539,799 discloses a test measurement body (2, FIGS. 1 and 2) for acceptance and stability testing of dental radiographic equipment. The test measurement body includes absorption elements (14) having varying X-ray absorption characteristics. Radiation from the X-ray source penetrates the test body and is detected by a sensor (3) which converts the detected radiation into electrical signals. The signals are fed into a computer (4) which then analyses the signals for deviations from a reference.

U.S. Pat. No. 5,544,157 describes a calibration template for producing standardized X-ray images. The template comprises an enclosure having materials of various shapes and densities to simulate the X-ray absorption properties of the human body, including bone, organs and other soft tissues.

These prior art systems rely on an X-ray source and a storage-phosphor screen as the image-producing components of a diagnostic procedure for testing and adjusting the imaging system. As such the quality and accuracy of the test is dependent on the condition and performance of these sub-systems. For example, test results are affected by X-ray dose accuracy and uniformity. The X-rays add quantum noise to the image. The image is dependent on the particular X-ray technique, which affects the X-ray energy and the amount of scatter. Finally, variations between X-rays sources affect uniformity of the tests.

The storage-phosphor screen also affects the test results. The construction of the screen itself affects resolution, noise and signal strength. Results vary among screens from different manufacturers and sometimes from the same manufacturer, even among different samples of the same screen model. Imperfections such as scratches and smudges on the surface cause artifacts which can affect the results. Finally, since the scanning process partially erases the stored image, each image must be exposed then scanned once and erased before the next image can be made, a time-consuming process that does not lend itself to repetition which makes adjustments and troubleshooting difficult to implement.

What is needed is a means of generating images for a CR system that does not involve the use of X-rays. It is also desirable to eliminate the storage-phosphor screen in order to eliminate certain variations inherent in their physical construction. What is needed therefore is apparatus which allows adjusting and testing of a CR system that avoids the potential inaccuracies and variations caused by the X-ray sub-system and storage-phosphor screen.

SUMMARY OF THE INVENTION

A method and apparatus for determining image quality in a computed radiography (CR) system includes providing a test substrate having a test pattern disposed thereon. The substrate includes material which fluoresces in the presence of the stimulating beam of the CR system. The test substrate is disposed in place of the storage-phosphor screen of the CR system. The stimulating beam scans the test substrate as if reading out an image stored in an exposed storage-phosphor screen. The fluorescent material in the test substrate produces stimulated emissions which are then detected by the CR detection system. The resulting image is compared against the test pattern. In this way, the imaging subsystem of the CR device can be calibrated, diagnosed for problems, and routinely monitored for accuracy, without the need or use of X-ray systems or storage-phosphor screens.

In a preferred embodiment, the test substrate is a colored paper or plastic sheet having dye which fluoresces in the presence of the stimulating beam. A pattern is printed on the substrate, obscuring portions of the paper and leaving exposed other portions of the underlying fluorescent dye, resulting in a fluorescent test pattern. In an alternate embodiment, an overlay containing a pattern is laminated atop the colored substrate to produce the fluorescent test pattern. In yet another embodiment, a non-fluorescing substrate is printed with a pattern using an ink containing fluorescent dye.

BEST MODE FOR CARRYING OUT THE INVENTION

Figure 1:
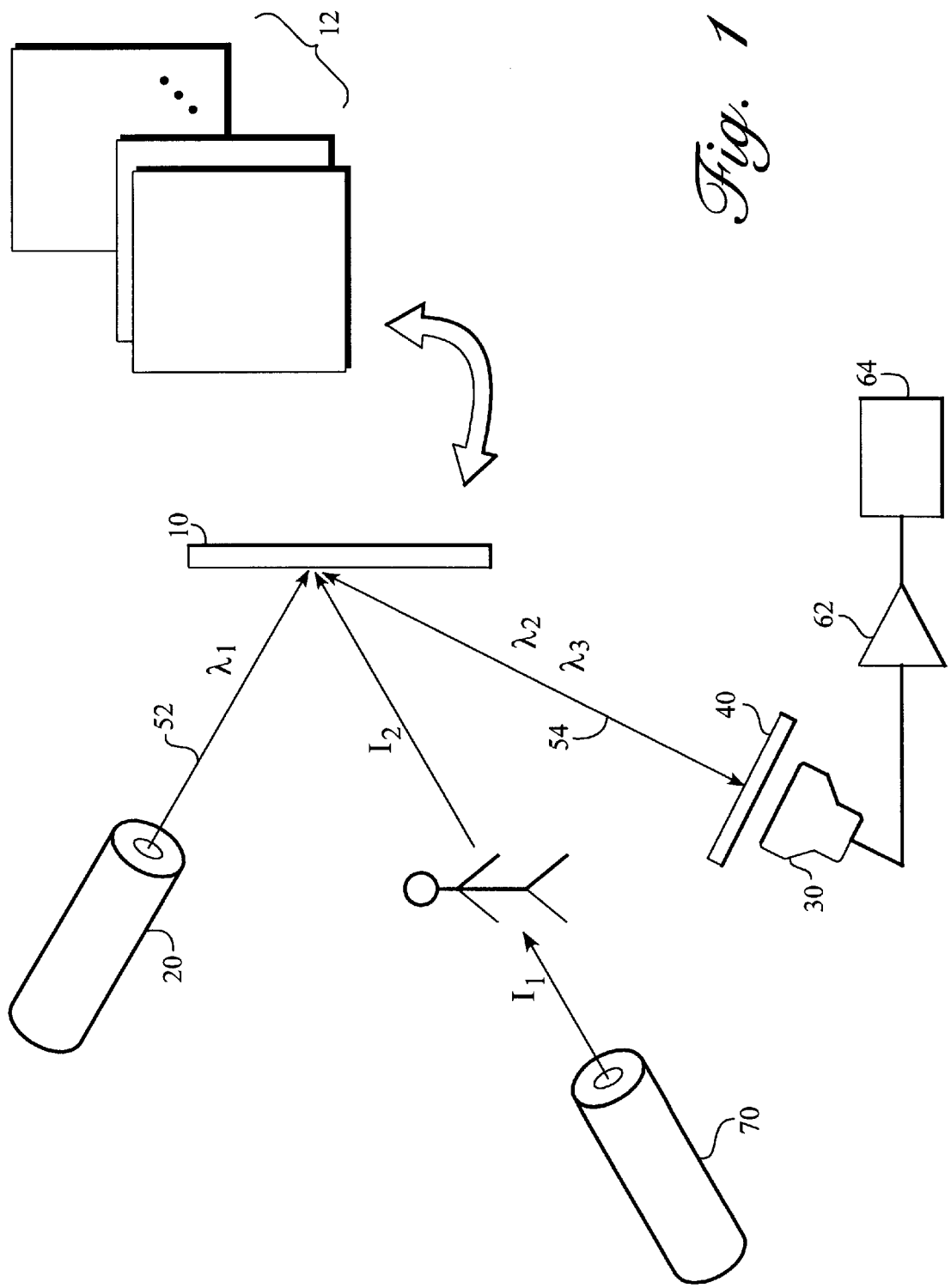
FIG. 1 is a schematic representation of a computed radiography (CR) system in accordance with the present invention.

Referring to FIG. 1, a computed radiography system 100 in accordance with the present invention includes an imaging source 70, typically an X-ray source. X-ray radiation emitted by source 70 passes through the object to be imaged, typically a human subject. As the X-ray radiation passes through the various tissues in the body, the radiation is attenuated as some of it is absorbed by the tissue. Consequently, the intensity of the X-ray radiation exiting the body will vary in accordance with the absorptive properties of the tissues encountered.

The X-ray radiation exiting the body is directed to a storage-phosphor screen 10. The material comprising screen 10 absorbs the X-ray radiation which excites its atomic constituents into higher energy states in proportion to the energy of the incident X-ray radiation and in so doing effectively stores a representation of the attenuation pattern of the X-ray radiation which constitutes an image of the object. It is a property of storage-phosphor screens that the excited atoms remain in their excited states and so the image persists.

In order to read-out the image from screen 10, a laser diode source 20 provides a stimulating beam of radiation 52 which is scanned across the screen. In a typical CR system, the stimulating wavelength $\lambda_1$ is between 630 nm and 680 nm (red). Storage screen 10 emits luminescent radiation 54 in response to scanning beam 53. The response wavelength $\lambda_2$ of commercially available storage-phosphor screens is in the range between 350 nm and 450 nm (blue-green).

Figure 2:
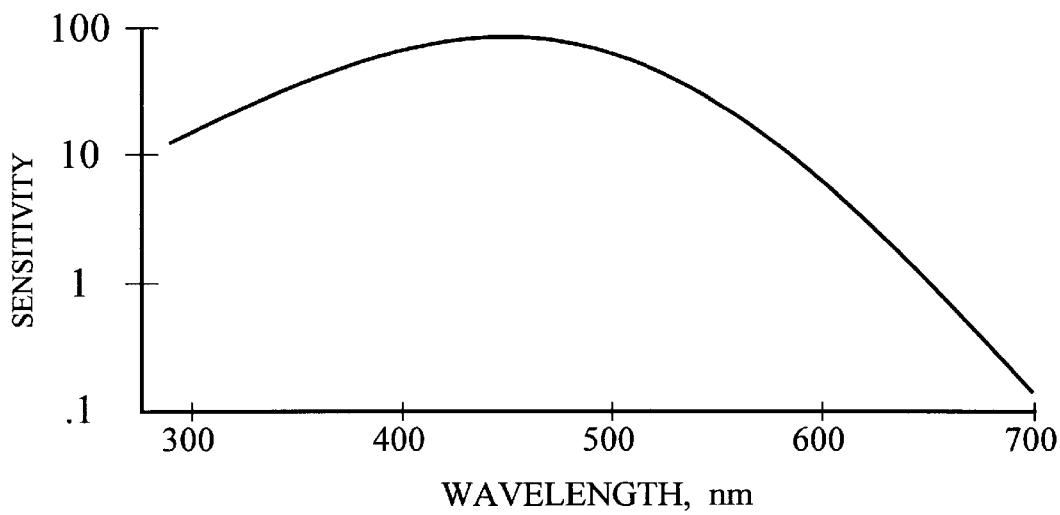
FIGS. 2–4 show spectral response curves of various components of a CR system.

The luminescent radiation 54 is directed through a glass filter 40 and detected by a photomultiplier tube (PMT) 30. Commercially available PMTs typically have a response range between 280 nm and 700 nm. Turning for a moment to FIG. 2, for example, the spectral response curve for a Photocathode Type 400K photomultiplier tube manufactured by Hamamatsu Corp. is shown. As can be seen, the radiant sensitivity of the photomultiplier tube between 300 nm and 700 nm varies from 10 mA/W to 0.1 mA/W.

Figure 3:
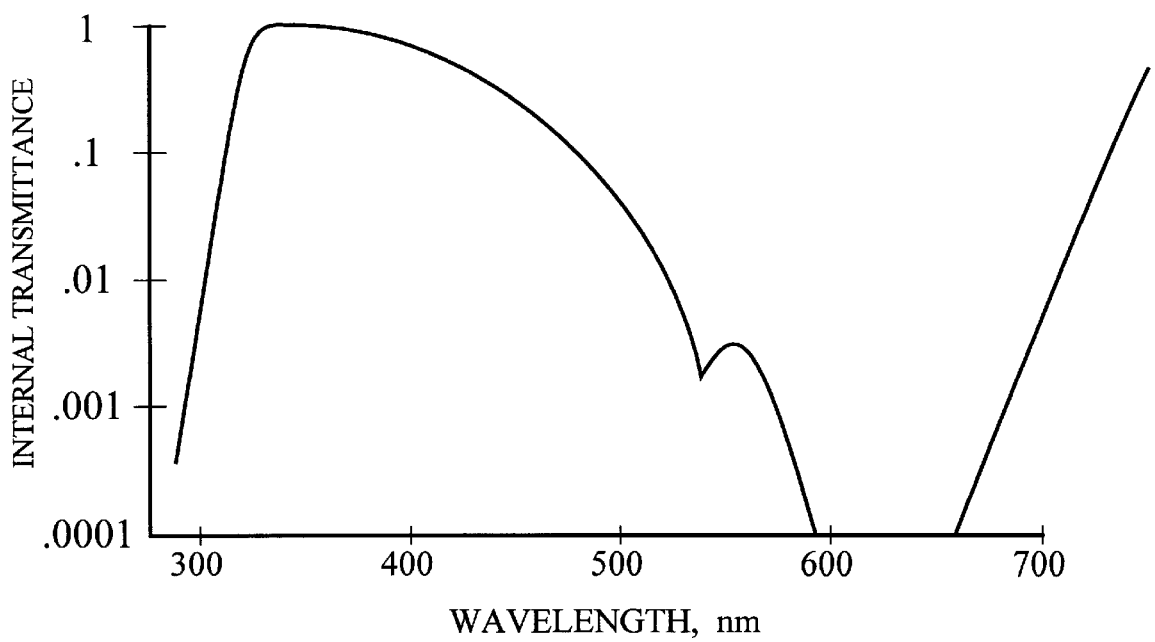
Figure 4:
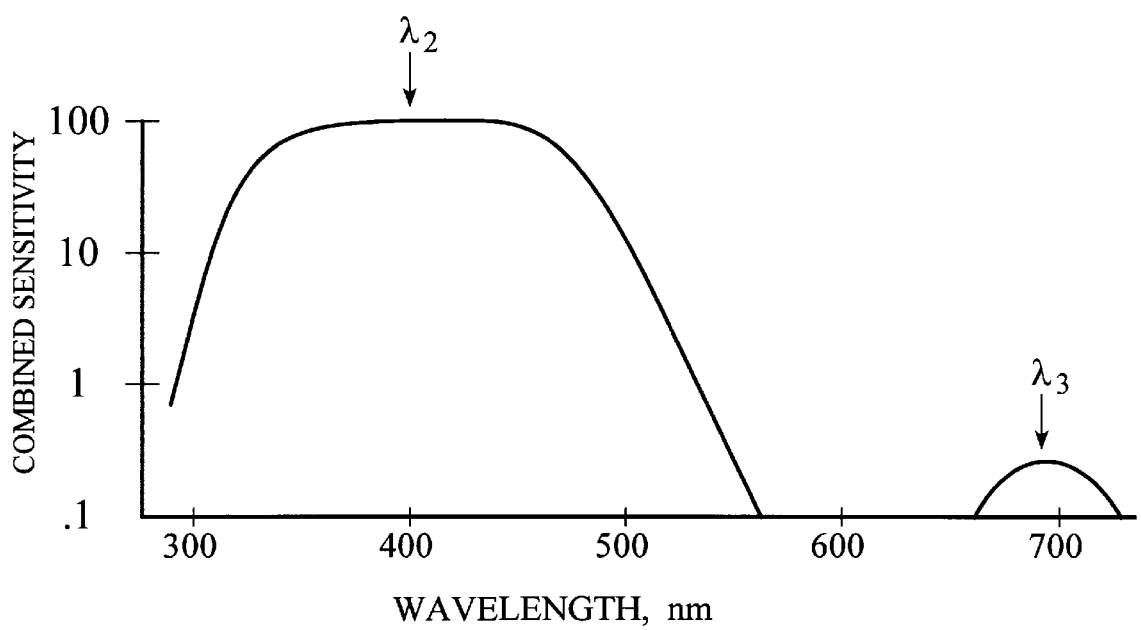

Returning to FIG. 1, a glass filter 40 is positioned in front of the detecting window of PMT 30. In the preferred embodiment, a laser diode with an output wavelength of approximately 650 nm and a Schott BG-3 or BG-4 type glass filter is used. The internal transmittance for the BG-3 glass filter is shown in FIG. 3. The graph shows that the filter blocks out light approximately in the range between 600 nm and 650 nm, thus rendering PMT 30 to be sensitive to wavelengths of light between the range 280 nm and 600 nm and to wavelengths beyond 650 nm. Glass filter 40 thus acts to substantially eliminate the detection of stimulating beam 52, since the wavelength of the stimulating beam is between 630 nm and 655 nm, while permitting the detection of beam 54.

The output of PMT 30, an electronic signal, feeds into a signal conditioner 62 and then processed by an image subsystem 64. Typically, signal conditioner 62 includes circuitry to amplify the PMT signal and to provide a cleaned-up signal for subsequent processing. Image subsystem 64 typically comprises an analog-to-digital converter which feeds a digitized PMT signal into a computer to analyze and create an image. Imaging subsystem 64 may include a display to view the image, a data store such as a disk drive to store the image, and a printer to provide a hard copy of the image.

Figure 5:
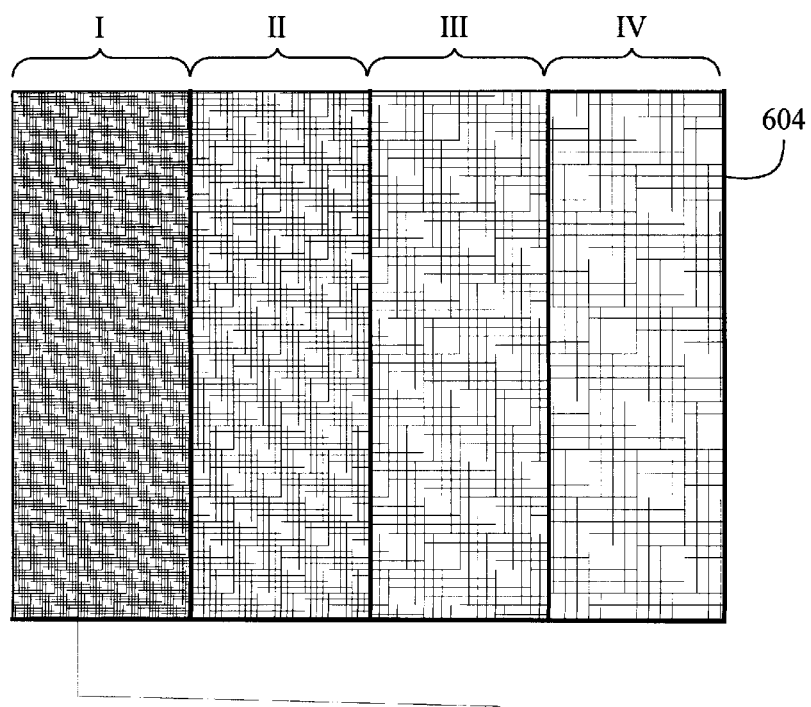
FIG. 5 shows a typical test pattern formed on exposed film.

Referring to FIG. 5, a spectral response curve is shown which represents the combined response of photomultiplier tube 30 and glass filter 40. A first region of sensitivity exists for wavelengths between 300 nm and approximately 600 nm, and a second region of sensitivity from 650 nm to 700 nm. Applicants discovered that certain colored papers and plastics use a dye which fluoresces in the 650 nm to 700 nm range when subjected to the stimulating radiation 52. One such colored paper is Astro Bright Rocket Red 65# cover stock manufactured by Wausau Papers, Inc. When scanned by the 630 nm to 680 nm wavelengths of the stimulating beam, this particular paper stock was found to fluoresce at $\lambda_3$, about 700 nm, with a signal strength of more than two orders of magnitude greater that the background signal. In the preferred embodiment, the paper is laminated to one or more backing layers to match the thickness of the storage-phosphor screen 10. An overcoat of clear plastic can be applied to the scanning surface for protection and enhanced laser absorption. Alternatively, a fluorescing dye can be embedded into a plastic substrate. One such dye is LD 700 manufactured by Exciton, Inc. of Dayton, Ohio. The plastic substrate can be of a thickness equal to the storage-phosphor screen, or provided with a backing layer to attain the desired thickness.

In accordance with the present invention, one or more of these substrates 12 (FIG. 1) are printed or silk-screened with a pattern. This will obscure portions of the underlying substrates and leave exposed the uneffected portions of the substrates, resulting in a fluorescent test pattern. One such patterned object is selected and disposed in place of storage screen 10. A read-out scanning operation is performed, and since the patterned object 12 is placed in the scan path instead of storage screen 10, the detector 30 will pick up the fluorescent emissions emanating from the scanned object. Moreover, since the detector/filter combination 30 and 40 is sensitive to wavelengths in the range between 650 nm to 700 nm, the wavelength $\lambda_3$ (650 nm to 700 nm) of the fluorescent emissions from the patterned object 12 will be captured by imaging subsystem 64. The resulting image can then be compared against the pattern 12 to determine the image forming quality of the CR system.

It has been found that common commercial printing techniques will produce usable patterns for the purpose of the invention. As such, any arbitrary pattern can be printed. Various useful patterns for test purposes include: A series of vertical bars of known and precise width and spacing. When this pattern is placed in the scanning path, the resulting signal clearly shows the dark/light differences, and the transitions can be used for aligning and testing the scan direction (X) scale and uniformity. Line-pair patterns of various intervals in both the X and the Y directions provide direct image data for quantitative evaluation of the spatial resolution of the system. Cross-hatched lines of known spacing enable the quantitative measurement of the geometric accuracy, including aspect ratio, of the entire image area. Diagonal lines provide a sensitive test of the coordination of the scanning control in the X and Y directions. Areas of dark in a surrounding lighter field and vice versa provide a test of the response of the system to abrupt, large changes in signal strength. Half-tone regions provide an approximation of variations in signal strength, similar to a step wedge image. A laser spot size of 175 microns would cover approximately 50 dots at 1200 dots per inch resolution, giving a range of 50:1.

As an alternative to printing, an exposed film can be laminated onto the substrate. The film can be exposed with the same patterns as described above for the printed patterns and laminated onto the colored paper to produce a test image substrate. In addition, the film can be exposed to known densities to provide a step wedge equivalent; e.g. FIG. 5 shows film 604 exposed to produce four regions of increasing density. Moreover, an exposed film can be laminated atop a substrate having a test pattern already printed on it. For example, the step wedges of FIG. 5 can be superposed atop a printed test pattern to produce patterns having a step wedge characterization.

Figure 6:
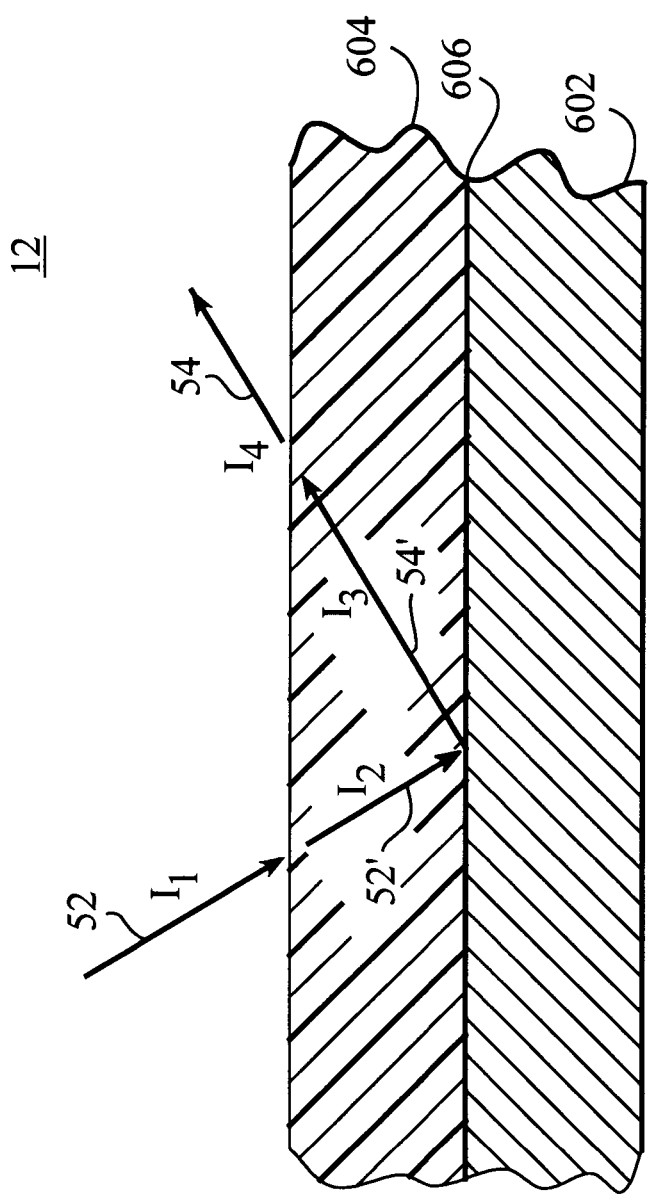
FIG. 6 is a cross-sectional view of a test pattern substrate.

As can be seen in FIG. 6, a test substrate 12 comprised of substrate 602 and a laminated exposed film 604 results in multiple attenuations of the stimulating diode laser. As can be seen, the intensity $I_1$ of stimulating beam 52 is attenuated to intensity level $I_2$, where $I_2<I_1$, upon entering laminate layer 604. The resulting fluorescent light 54' is attenuated upon exiting laminate layer 604. While this does not negatively impact the operation of the invention, it must be taken into consideration when analyzing the resulting image. As a final note, there is additional attenuation due to the presence of the glue layer 606 used to bind laminate 604 to colored paper 602 and due to the multiple reflective surfaces resulting from differences in their respective refractive indices.

As an alternative to using colored paper, the fluorescent pattern can be formed by using inks which contain the fluorescent material. In this case, the underlying substrate does not fluoresce. Rather, the ink itself fluoresces. While this method of forming the test pattern may not be as cost effective as the use of colored papers with printed patterns, the invention will nevertheless work just as well. Yet another alternative that will work in accordance with the invention is to print a pattern on fluorescent paper using a differently colored fluorescent dye.

The above-described invention has many advantages over existing systems which employ test objects requiring exposure to X-ray radiation. Firstly, the complications of setting up and using the X-ray equipment and the health risks involved are completely avoided. Contrary to prior art systems, the present invention obviates the need for storage-phosphor screens which require special light-tight cassettes and screen erasing systems. Inaccuracies due to variations in X-ray and screen characteristics are eliminated. The use of fluorescent papers and plastic sheets per the invention results in more uniform test patterns owing to mass production techniques for printing the test patterns. The low cost of such papers means that test patterns can be replaced on a regular basis to assure uniform results. Test images produced in accordance with the invention can be made more easily and rapidly because exposure and erasing of plates is not required. This makes practical regularly scheduled quality assurance measurements on the system. Repetitive signals can be generated since the scanning is nondestructive. This is useful for adjustments and diagnosis.

What is claimed is:

1. In a computed radiography system having a storage screen, a stimulating source for scanning said storage screen to read out a stored image and a detector for detecting stimulated light emissions from said storage screen, a method for ascertaining image read-out quality comprising the steps of:

providing a fluorescent test pattern;

substituting said storage screen with said test pattern, thereby positioning said test pattern in a scan path of said stimulating source;

scanning said test pattern with said stimulating source to produce fluorescent emissions from said test pattern;

detecting said fluorescent emissions with said detector;

producing a read-out image based on said fluorescent emissions; and comparing said read-out image against said test pattern.

2. The method of claim 1 wherein said step of providing a test pattern includes providing a substrate having material which fluoresces in the presence of said stimulating source and printing said test pattern on said substrate.

3. The method of claim 2 further including providing a film atop said test pattern, said film having varying transmissivity from one area thereof to another.

4. The method of claim 1 further including providing a substrate having material which fluoresces in the presence of said stimulating source and wherein said step of providing a test pattern includes exposing a film to produce a pattern of light and dark regions and disposing said film atop said substrate.

5. The method of claim 1 wherein said step of providing a test pattern includes printing a pattern with an ink having material which fluoresces in the presence of said stimulating source.

6. The method of claim 1 further including providing a substrate containing a first dye which fluoresces in the presence of said stimulating source; wherein said step of providing a test pattern includes printing a pattern with an ink having a second dye which fluoresces in the presence of said stimulating source.

7. The method of claim 1 further including providing a plurality of fluorescent test patterns and selecting from among said plurality of test patterns.

8. In a computed radiography system comprising an X-ray source, a phosphor storage screen aligned with said X-ray source, a read-out stimulating source aligned to scan said storage phosphor screen, and a detector aligned to detect stimulated light emissions from said phosphor storage screen, a method for determining image read-out quality comprising the steps of:

(a) selecting a first substrate containing a dye which fluoresces in the presence of said read-out stimulating source;

(b) forming a first test pattern on said first substrate;

(c) disposing said first substrate in place of said phosphor storage screen;

(d) scanning said first substrate with said read-out stimulating source to produce fluorescent emissions from said first test pattern;

(e) detecting said fluorescent emissions;

(f) producing a first read-out image from said fluorescent emissions; and (g) comparing said first read-out image against said first test pattern to ascertain image read-out quality of said computed radiography system.

9. The method of claim 8 wherein said step of forming said first test pattern includes printing a pattern on said first substrate.

10. The method of claim 9 wherein said step of printing includes printing with an ink having a second dye which fluoresces in the presence of said read-out stimulating source.

11. The method of claim 9 further including providing a film, having varying transmissivity to said read-out stimilating source from one area thereof to another, atop said first substrate.

12. The method of claim 8 wherein said step of forming said first test pattern includes providing a film, having varying transmissivity to said read-out stimulating source from one area thereof to another, atop said first substrate.

13. The method of claim 8 wherein said step of forming said first test pattern includes exposing a film with a pattern and disposing said film atop said first substrate.

14. The method of claim 8 further including forming a second test pattern on said first substrate.

15. The method of claim 8 further including forming a second test pattern on a second substrate and repeating said steps (c) through (g) using said second substrate.

16. A computed radiography system comprising:

first and second stimulating sources;

a first imaging medium having a storage phosphor layer and a second imaging medium having a having a fluorescent layer containing a material which fluoresces in the presence of said second stimulating source; and a detector;

said first stimulating source and said first imaging medium having a first selectable alignment whereby emissions from said first stimulating source are directed upon said first imaging medium to expose said storage phosphor layer thereby retaining an image thereon;

said second stimulating source and said first imaging medium having a second selectable alignment whereby emissions from said second stimulating source are directed upon said first imaging medium to produce first stimulated emissions from said storage phosphor layer;

said second imaging medium being selectively disposed in place of said first imaging medium whereby said emissions from said second stimulating source are directed upon said second imaging medium to produce second stimulated emissions from said fluorescent layer;

said detector aligned to receive said first and second stimulated emissions.

17. The system of claim 16 wherein said second imaging medium is a paper containing a dye which fluoresces in the presence of said second stimulating source.

18. The system of claim 17 wherein said second imaging medium includes a pattern obscuring first portions of said paper and leaving exposed second portions of said paper.

19. The system of claim 16 wherein said second imaging medium includes a second layer disposed atop said fluorescent layer, said second layer having regions of different transmissivity to said second stimulating source.

20. The system of claim 19 wherein said second layer is an exposed film.

21. The system of claim 16 wherein said fluorescent layer includes first and second patterns.

22. The system of claim 16 wherein said second imaging medium includes a pattern of fluorescent ink which fluoresces in the presence of said second stimulating source.

* * * * *